United States Patent [19]

Nonogaki et al.

[11] Patent Number: 4,728,594
[45] Date of Patent: Mar. 1, 1988

[54] PHOTOSENSITIVE COMPOSITION WITH AZIDE OR BISAZIDE COMPOUND WITH OXAZOLONE GROUP

[75] Inventors: Saburo Nonogaki; Ryotaro Irie, both of Tokyo; Michiaki Hashimoto, Sayama; Takao Iwayanagi, Tokyo, all of Japan

[73] Assignee: Hitachi Chemical Co., Ltd., Japan

[21] Appl. No.: 818,686

[22] Filed: Jan. 14, 1986

[30] Foreign Application Priority Data

Jan. 18, 1985 [JP] Japan .................... 60-5756

[51] Int. Cl.⁴ .................... G03C 1/52; G03C 1/71
[52] U.S. Cl. .................... 430/197; 260/349; 430/194; 430/325; 430/927
[58] Field of Search ........ 430/197, 325, 194, 927; 260/349

[56] References Cited

U.S. PATENT DOCUMENTS

| | | | |
|---|---|---|---|
| 2,848,328 | 8/1958 | Hepher | 430/197 |
| 3,475,176 | 10/1969 | Rauner et al. | 430/197 |
| 3,595,656 | 7/1971 | Ruckert et al. | 430/197 |
| 3,721,566 | 3/1973 | Laridon et al. | 430/197 |
| 3,856,531 | 12/1974 | Guisdale et al. | 430/196 |
| 4,086,209 | 4/1978 | Hara et al. | 528/125 |
| 4,191,571 | 3/1980 | Nonogaki et al. | 430/325 |
| 4,308,341 | 12/1981 | DoMill | 430/179 |
| 4,565,768 | 1/1986 | Nonogaki et al. | 430/194 |

FOREIGN PATENT DOCUMENTS 53-34902  7/1970  Japan .................... 430/197

OTHER PUBLICATIONS

Kosar, J., "Light-Sensitive Systems, J. Wiley & Sons, 1965, pp. 330-336.

*Primary Examiner*—Charles L. Bowers, Jr.
*Attorney, Agent, or Firm*—Antonelli, Terry & Wands

[57] ABSTRACT

A photosensitive composition comprising an azide compound represented by the formula:

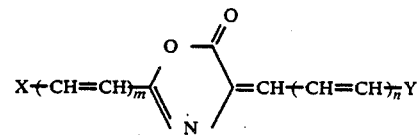

wherein each of X and Y is an aromatic substituent group, at least one of X and Y being an aromatic substituent group having an azide group, and n and m are zeros or integers of 1, and a polymeric compound. Since this composition has high resolution and is photosensitive to light having a wavelength of 436 nm, it permits employment of a reduction projection printer and is suitable for fabrication of semiconductor devices.

6 Claims, No Drawings

PHOTOSENSITIVE COMPOSITION WITH AZIDE OR BISAZIDE COMPOUND WITH OXAZOLONE GROUP

BACKGROUND OF THE INVENTION

This invention relates to a photosensitive composition. Particularly, it relates to a photoresist (a photosensitive, etching-resistant coating material) having high resolution which is suitable for fabricating semiconductor devices.

For improving the performance characteristics of semiconductor devices such as IC, LSI and the like, it is necessary to improve the fineness of their fabrication. Therefore, a photoresist used for the fabrication is required to have particularly high resolution.

As is generally known, photoresists are divided into two groups, i.e., positive type and negative type. Almost all of positive type photoresists used for fabricating semiconductor devices are obtained by mixing an alkali-soluble phenolic resin as a film-forming component with a naphthoquinone diazide derivative as a photosensitive component. Almost all of negative type photoresists used for fabricating semiconductor devices are obtained by mixing a cyclized rubber with an aromatic bisazide as a photosensitive component.

When there is made a comparison between the resolutions of the above-mentioned two kinds of photoresists, the resolution of the positive type photoresists is superior to that of the negative type photoresists. Therefore, the positive type photoresists have come to be often used for recent fabrication of high-performance semiconductor devices.

The reason why the resolution of the positive type photoresists is higher than that of the negative type photoresists is as follows. The contrast of the positive type photoresists is higher than that of the negative type photoresists and the positive type photoresists are developed without their swelling with a developer. On the other hand, the negative type photoresists are swollen with a developer, so that their patterns are lost or deformed in some cases.

Accordingly, the negative type photoresists also can be expected to have high resolution if their contrast is high and they are not swollen with a developer.

Among photoresists used for uses other than fabrication of semiconductor devices, there are known negative type photoresists which are not swollen with a developer. For example, it is well known that a mixture of an alkali-soluble phenolic resin and an aromatic azide can be utilized as a negative type photoresist for fabrication of photographic printing plates, and this photoresist does not undergo swelling phenomenon when developed with an aqueous alkali solution. Japanese Patent Publication No. 22082/70 discloses a negative type photoresist containing an aromatic azide compound and an alkali-soluble phenol-formaldehyde resin, and Japanese Patent Publication No. 34902/78 discloses a negative type photoresist containing an aromatic azide compound and a polymer of hydroxystyrene.

However, few cases are known where these photoresists are utilized for fabricating semiconductor devices. The reason for this is that these photoresists have been developed mainly for the purpose of utilizing them for fabrication of photographic printing plates, and are suitable for utilization in the form of a coating film having a thickness of several tens microns but have not always been suitable for utilization in the form of a coating film which has a thickness of several microns to about 0.1 micron like a coating film used in fabrication process of semiconductor devices.

Further, for improving the performance characteristics of a semiconductor device, micro-fabrication is necessary, therefore in fabricating a semiconductor device, a fine pattern of photoresist is often formed by using a reduction projection printer. Usually, the optics of a reduction projection printer do not transmit UV light but transmit the light with wavelengths longer than 400 nm. The wavelengths of light of a high pressure Hg lamp as a light source include 405 nm, 436 nm, etc. in the visible region, and light having a high intensity is one which has a wavelength of 436 nm, i.e., light called "g-line". Accordingly, only photoresists which are hardened by this light having the wavelength of 436 nm permit employment of a reduction projection printer. The above-mentioned conventional negative photoresists are hardly photosensitive to the light having the wavelength of 436 nm and are not hardened thereby.

SUMMARY OF THE INVENTION

An object of this invention is to provide a photoresist which has high resolution and is photosensitive to the light having the wavelength of 436 nm.

This invention provides a photosensitive composition comprising an azide compound represented by the formula;

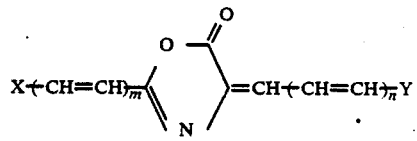

wherein each of X and Y is an aromatic substituent group, at least one of X and Y being an aromatic substituent group having an azide group, and n and m are zeros or integers of 1, and a polymeric compound.

DETAILED DESCRIPTION OF THE PREFERRED EMBODIMENTS

As described above, in fabricating a semiconductor device, a photoresist is often used in the form of a coating film having a thickness of several microns to about 0.1 micron. For conducting insolubilization reaction by irradiation with light effectively also in such a thin coating film and preventing therein the quality of optical image from being lowered by halation from a substrate as a support for the film, it is necessary that the aromatic azide in the film should strongly absorb the light incident on the film. As described above, this light is one which has the wavelength of 436 nm.

Further, a photoresist is usually handled in the form of a solution prepared by dissolving it in a suitable organic solvent. Therefore, the aromatic azide which should be contained in the photoresist in a high concentration should be soluble also in the solvent for the photoresist in a high concentration.

From all these facts, it can be seen that the photosensitive component of a negative type photoresist suitable for fabrication of semiconductor devices is preferably one which is highly soluble in a solvent used as the solvent for the photoresist solution and strongly absorbs the light having the wavelength of 436 nm.

The present inventors synthesized a group of novel aromatic azides which satisfied the above-mentioned conditions sufficiently and was inexpensive, and could obtain, by use of said aromatic azide, a negative type photoresist having high resolution which is suitable particularly for fabrication of semiconductor devices.

The photosensitive composition of this invention comprises an azide compound represented by the formula:

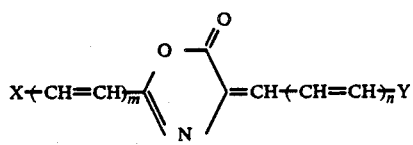

wherein each of X and Y is an aromatic substituent group, at least one of X and Y being an aromatic substituent group having an azide group, and n and m are zeros or integers of 1, and a polymeric compound.

It is preferable that either or both of X and Y in the above general formula are azidophenyl groups. When either X or Y is an aromatic substituent group having an azide group, there are used azide compounds in which the other substituent group is a phenyl group, methoxyphenyl group, acetoxyphenyl group, aminophenyl group, (acetylamino)phenyl group, (dimethylamino)phenyl group, pyridyl group, thienyl group, furyl group or the like. Needless to say, the other substituent group may be other than these substituent groups. As the aromatic substituent group having an azide group, those formed by bonding an azide group to the above-mentioned aromatic substituent groups are preferably chosen.

These compounds are equimolarly condensed compounds from a carboxylic acid and an aldehyde represented by the formulas:

respectively, wherein X, Y, m and n have the same meanings as defined above. They can be obtained by condensation of the two compounds.

The amount of the azide compound is preferable in the range of 0.5 to 100% by weight, more preferably 1 to 50% by weight based on the weight of the polymeric compound. When it is less than 0.5% by weight, the sensitivity is low, while when it exceeds 100% by weight, the characteristics of coating film are deteriorated.

As the polymeric compound, there are preferably used polymers or copolymers of hydroxystyrene, partly denatured polymers or copolymers of hydroxystyrene, and phenolic resins such as products of condensation of phenol derivatives with formaldehyde. There can be also used natural rubber; denatured rubbers such as cyclized natural rubber and the like; synthetic rubbers such as polybutadiene, polyisoprene, cyclized polybutadiene, cyclized polyisoprene, styrene-butadiene rubber and the like; synthetic polymer compounds such as polystyrene, iodinated polystyrene, poly(vinyl butyral), poly(methyl methacrylate), poly(glycidyl methacrylate), poly(methyl isopropenyl ketone) and the like; etc.

These polymeric compounds are dissolved in a solvent together with a photosensitive azide compound of the above general formula to obtain a photosensitive composition. As the solvent, there can be used depending on the kind and use of the composition and the like, for example, ketones such as cyclohexanone, methyl isobutyl ketone and the like; aromatic hydrocarbons such as xylene; chlorobenzene and the like; Cellosolve acetate derivatives such as methyl Cellosolve acetate, ethyl Cellosolve acetate and the like; Cellosolve derivatives such as ethyl Cellosolve, butyl Cellosolve and the like; esters of acetic acid such as butyl acetate, amyl acetate and the like; dimethylformamide; dimethylacetamide; etc.

This invention is further illustrated in more detail by way of the following Examples.

First, some compounds were selected from the group of novel azide compounds. In Table 1 are shown their respective structures (represented by m, n, X and Y in the above formula), numbers assigned to the structures for explanation, and two physical properties of the compounds, i.e., the wavelength of maximum absorption in the UV-vis.spectrum in a methanol solution and the wavenumber of antisymmetric stretching vibration in azide group in the infrared absorption spectrum.

TABLE 1

| No. | m | n | Structure X | Y | Wavelength of maximum absorption (nm) | IR (—N$_3$) (cm$^{-1}$) |
|-----|---|---|---|---|---|---|
| I | 0 | 0 | phenyl | 4-azidophenyl | 381 | 2130 |
| II | 0 | 0 | 4-azidophenyl | phenyl | 374 | 2160 |
| III | 0 | 0 | 4-azidophenyl | 4-azidophenyl | 393 | 2140 |

TABLE 1-continued
| No. | m | n | Structure X | Y | Wavelength of maximum absorption (nm) | IR (—N₃) (cm⁻¹) |
|---|---|---|---|---|---|---|
| IV | 0 | 0 | 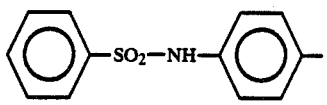 | 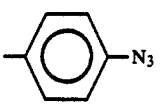 | 391 | 2120 |
| V | 0 | 0 | 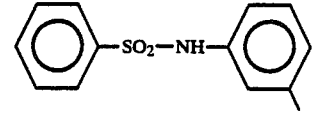 | 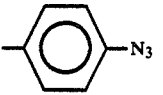 | 384 | 2120 |
| VI | 0 | 0 | 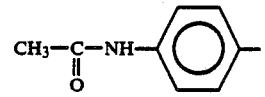 | 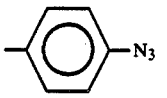 | 394 | 2130 |
| VII | 0 | 0 | 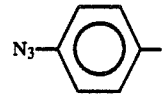 | 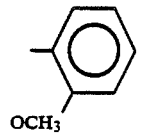 | 394 | 2150 |
| VIII | 0 | 0 | 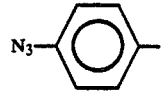 | 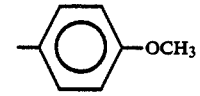 | 392 | 2140 |
| IX | 0 | 0 | 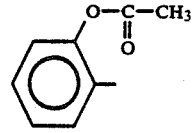 | 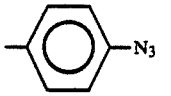 | 386 | 2120 |
| X | 0 | 0 | 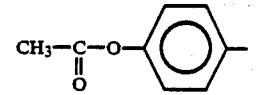 | 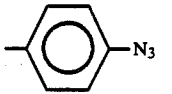 | 382 | 2120 |
| XI | 0 | 0 | 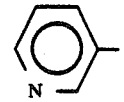 | 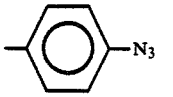 | 385 | 2120 |
| XII | 0 | 0 |  | 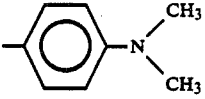 | 447 | 2145 |
| XIII | 0 | 0 | 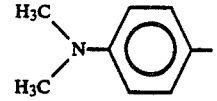 | 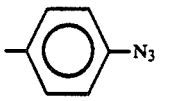 | 441 | 2120 |
| XIV | 0 | 1 |  | 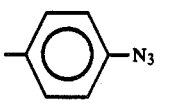 | 408 | 2125 |
| XV | 0 | 1 | 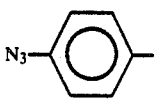 |  | 394 | 2140 |

TABLE 1-continued

| No. | m | n | Structure X | Y | Wavelength of maximum absorption (nm) | IR (—N₃) (cm⁻¹) |
|---|---|---|---|---|---|---|
| XVI | 0 | 1 | 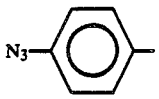 | 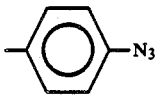 | 412 | 2140 |
| XVII | 0 | 1 | 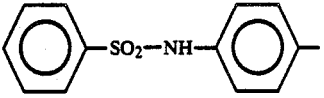 | 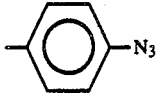 | 415 | 2120 |
| XVIII | 1 | 0 | 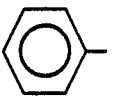 | 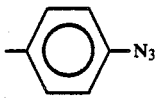 | 405 | 2110 |
| XIX | 1 | 1 | 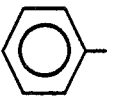 | 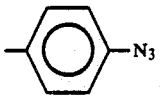 | 433 | 2120 |
| XX | 0 | 0 | 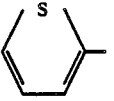 | 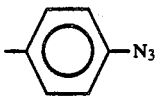 | 394 | 2120 |
| XXI | 0 | 0 | 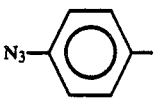 | 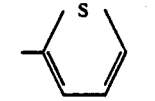 | 398 | 2150 |
| XXII | 0 | 1 | 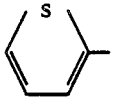 | 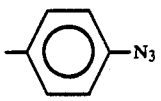 | 414 | 2120 |

By use of the above-mentioned numbers, photosensitive azide compounds having the structures corresponding to the numbers are named azide I, azide II, azide III and so on. Examples are shown below for the individual azide compounds.

EXAMPLE 1

First, synthesis of azide I [2-phenyl-4-(p-azidobenzylidene)-5(4)-oxazolone] is shown below.

With 2 g of N-benzoylglycine were mixed 1.64 g of P-azidobenzaldehyde, 1.6 g of sodium acetate and 4 ml of acetic anhydride, and the resulting mixture was heated for 15 minutes by immersing the vessel in hot water. The mixture became a yellow mass of crystals. Ethanol was added to the mixture to obtain a suspension, and the yellow crystals were separated from the mother liquor by filtration, washed with hot water, and dried to obtain an azide compound (azide I) having an azlactone ring. This azide I had a wavelength of maximum absorption of 381 nm in methanol.

Next, preparation of a resist by use of azide I and confirmation of its photosensitivety are shown below.

A resist solution having the following composition was prepared:

| | |
|---|---|
| Polyvinylphenol (Resin M, Maruzen Oil Co., Ltd.) | 2.3% by weight |
| Azide I | 0.6% by weight |
| Cyclohexanone | 97.1% by weight |

This solution was spin-coated on a silicon wafer having a diameter of 3 inches at 100 r.p.m. (rotation per minute), and heated at 80° C. for 20 minutes to evaporate the cyclohexanone, whereby a resist film of 0.3 μm in thickness was formed. The film was placed at a distance of 50 cm from a 600 W Xe-Hg lamp and exposed to light having a wavelength longer than 430 nm through a UV cutoff filter V-Y43 (Toshiba) to print a pattern. The exposed film was developed with a tetramethylammonium hydroxide (0.79%) aqueous solution at 24° C. for 105 seconds. This film was not swollen with the developer and had high resolution. When the exposure time was 50 seconds, a slight pattern of resist film was observed. On the other hand, when it was 100 seconds, a clear negative pattern of resist film was obtained.

The wavelength of maximum photo-absorption of a film formed by coating the aforesaid resist solution on a quartz plate to a thickness of 0.2 μm was 394 nm and the absorbance at this wavelength was 0.6.

EXAMPLE 2

First, synthesis of azide II [2-(p-azidophenyl)-4-benzylidene-5(4)-oxazolone] is shown below.

An azide compound (azide II) having an azlactone ring was obtained from equimolar amounts of p-azidohippuric acid and benzaldehyde in the same manner as in Example 1. This azide II had a wavelength of maximum photo-absorption at 374 nm in methanol.

Next, preparation of a resist by use of azide II and confirmation of its photosensitivity are shown below.

A resist solution having the following composition was prepared:

| | |
|---|---|
| Polyvinylphenol (Resin M, Maruzen Oil Co., Ltd.) | 2.3% by weight |
| Azide II | 0.6% by weight |
| Cyclohexanone | 97.1% by weight |

This solution was spin-coated on a silicon wafer having a diameter of 3 inches at 100 r.p.m. with infrared radiation, and the cyclohexanone was evaporated to form a resist film of 0.9 μm in thickness. The film was placed at a distance of 50 cm from a 600 W Xe-Hg lamp and exposed to light having a wavelength longer than 430 nm through a UV cut-off filter V-Y43 (Toshiba) to print a pattern. The exposed film was developed with a tetramethylammonium hydroxide (0.79%) aqueous solution at 24° C. for 105 seconds. When the exposure time was 100 seconds, a slight pattern of resist film was observed, while when it is 500 seconds, a clear negative pattern of resist film was obtained. Said film was not swollen with the developer either and had high resolution.

The wavelength of maximum photo-absorption of a film formed by coating the aforesaid resist solution on a quartz plate was 386 nm.

EXAMPLE 3

First, synthesis of azide III [2-(p-azidophenyl)-4-(p-azidobenzylidene)-5(4)-oxazolone] is shown below.

An azide compound (azide III) having an azlactone ring was obtained from equimolar amounts of p-azidohippuric acid and p-azidobenzaldehyde in the same manner as in Example 1. This azide III had a wavelenth of maximum photo-absorption at 393 nm in methanol.

Next, preparation of a resist by use of azide III and confirmation of its photosensitivity are shown below.

A resist solution having the following composition was prepared:

| | |
|---|---|
| Cyclized polyisoprene | 9.09% by weight |
| Azide III | 0.05% by weight |
| Chlorobenzene | 90.86% by weight |

This solution was spin-coated on a silicon wafer having a diameter of 3 inches at 3,000 r.p.m., and heated at 80° C. for 20 minutes to evaporate the chlorobenzene, whereby a resist film of 1.2 μm in thickness was formed. The film was placed at a distance of 50 cm from a 600 W Xe-Hg lamp and exposed to print a pattern. The exposed film was developed with xylene for 30 seconds. When the exposure time was 50 seconds, a slight pattern of resist film was observed, while when it is 200 seconds, a clear negative pattern of resist film was obtained.

The wavelength of maximum photo-absorption of a film formed by coating the aforesaid resist solution on a quartz plate to a thickness of 0.5 μm was 402 nm and the absorbance at this wavelength was 0.04.

EXAMPLE 4

First, synthesis of azide IV [2-(p-(N-phenylsulfonylamino)phenyl)-4-(p-azidobenzylidene)-5(4)-oxazolone] is shown below.

An azide compound (azide IV) having an azlactone ring was obtained from equimolar amounts of p-(N-phenylsulfonylamino)hippuric acid and p-azidobenzaldehyde in the same manner as in Example 1. This azide IV had a wavelength of maximum photo-absorption at 391 nm in methanol.

Next, preparation of a resist by use of azide IV and confirmation of its photosensitivity are shown below.

A resist solution having the following composition was prepared:

| | |
|---|---|
| Polyvinylphenol (Resin M, Maruzen Oil Co., Ltd.) | 4.7% by weight |
| Azide IV | 2.0% by weight |
| Cyclohexanone | 93.3% by weight |

This solution was spin-coated on a silicon wafer having a diameter of 3 inches at 100 r.p.m. with infrared radiation, and the cyclohexanone was evaporated to form a resist film of 0.66 μm in thickness. The film was placed at a distance of 50 cm from a 600 W Xe-Hg lamp and exposed to light having a wavelength longer than 430 nm through a UV cut-off filter V-Y43 (Toshiba) to print a pattern. The exposed film was developed with a tetramethylammonium hydroxide (0.60%) aqueous solution at 24° C. for 135 seconds. When the exposure time was 10 seconds, a slight pattern of resist film was observed, while when it was 50 seconds, a clear negative pattern of resist film was obtained. Said film was not swollen with the developer and had high resolution.

The wavelength of maximum photo-absorption of a film formed by coating the aforesaid resist solution on a quartz plate to a thickness of 0.66 μm was 403 nm and the absorbance at this wavelength was 1.8.

EXAMPLE 5

First, synthesis of azide XI [2-(m-pyridyl)-4-(p-azidobenzylidene)-5(4)-oxazolone] is shown below.

With 12.3 g of nicotinic acid was mixed 17.0 g of thionyl chloride, and the resulting mixture was allowed to stand at room temperature for 40 minutes to obtain a white solid. In 50.0 g of water were dissolved 22.5 g of glycine and 12.0 g of sodium hydroxide to obtain a homogeneous solution, which was then mixed with the aforesaid white solid. The resulting mixture generated heat vigorously and then became white paste. After 300 g of water was added to the paste, the precipitate formed was separated from the mother liquor by filtration and dried to obtain 4.0 g of white powder. The powder was impure nicotinylglycine.

The whole of the powder, 3.5 g of p-azidobenzaldehyde, 2.0 g of sodium acetate (anhydrous) and 8 ml of acetic anhydride were mixed and then heated for 15 minutes by immersing the vessel in hot water. The mixture became yellowish-orange-colored paste. After 40 ml of methanol was added to this mixture, the yellow crystals formed were separated from the mother liquor by filtration, washed with a sodium hydrogencarbonate aqueous solution and then with water, and dried to obtain a crude azide compound (azide XI) having an azlactone ring. The crude azide compound was recrystallized from acetone to obtain 0.3 g of pure azide XI.

This azide XI exhibited, in methanol, a maximum absorption with an absorbance of $3.8 \times 10^4$ cm$^{-1}$·liter·mol$^{-1}$ at a wavelength of 385 nm and a shoulder of absorption with an absorbance of $3.3 \times 10^4$ cm$^{-1}$·liter·mol$^{-1}$ at a wavelength of 401 nm.

Next, preparation of a resist by use of azide XI and confirmation of its photosensitivity are shown below.

A resist solution having the following composition was prepared:

| | |
|---|---|
| Polyvinylphenol (Resin M, Maruzen Oil Co., Ltd.) | 7.5% by weight |
| Azide XI | 1.5% by weight |
| Cyclohexanone | 91.0% by weight. |

This solution was spin-coated on a silicon wafer having a diameter of 3 inches at 200 r.p.m., and the cyclohexanone was evaporated by drying with infrared radiation to form a resist film of 1.1 μm in thickness. The film was placed at a distance of 60 cm from a 500 W high pressure Hg lamp and exposed to the monochrome light ($\lambda=436$ nm) transmitted by the combination of UV cut-off filter and interference filter, namely, g-line to print a pattern.

The exposed film was developed with a tetramethylammonium hydroxide (1.19%) aqueous solution at 23° C. for 40 seconds. When the exposure time was 3 minutes, a slight pattern of resist film was observed, while it was 6 minutes, a clean negative pattern of resist film was obtained. Said film also was not swollen with the developer and had high resolution.

The absorbance at a wavelength of 436 nm of a film formed by coating the aforesaid resist solution on a quartz plate under the same coating conditions as described above was 1.3.

EXAMPLE 6

First, synthesis of azide XIV [2-phenyl-4-(p-azidocinnamylidene)-5(4)-oxazolone] is shown below.

An azide compound (azide XIV) having an azlactone ring was obtained from equimolar amounts of hippuric acid and p-azidocinnamaldehyde in the same manner as in Example 1. This azide XIV had a wavelength of maximum photoabsorption at 408 nm in methanol.

Next, preparation of a resist by use of azide XIV and confirmation of its photosensitivity are shown below.

A resist solution having the following composition was prepared:

| | |
|---|---|
| Polyvinylphenol (Resin M, Maruzen Oil Co., Ltd.) | 5.3% by weight |
| Azide XIV | 1.3% by weight |
| Cyclohexanone | 93.4% by weight. |

This solution was spin-coated on a silicon wafer having a diameter of 3 inches at 200 r.p.m. and the cyclohexanone was evaporated to form a resist film of 0.5 μm in thickness. The film was placed at a distance of 50 cm from a 600 W Xe-Hg lamp and exposed to light having a wavelength longer than 430 nm through a UV cut-off filter V-Y43 (Toshiba) to print a pattern. The exposed film was developed with a tetramethylammonium hydroxide (0.95%) aqueous solution at 24° C. for 115 seconds. When the exposure time was 10 seconds, a slight pattern of resist film was observed, while when it was 20 seconds, a clear negative pattern of resist film was obtained at high resolution without swelling.

The wavelength of maximum photo-absorption of a film formed by coating the aforesaid resist solution on a quartz plate to a thickness of 0.2 μm was 422 nm and the absorbance at this wavelength was 0.47.

EXAMPLE 7

First, synthesis of azide XV [2-(p-azidophenyl)-4-cinnamylidene-5(4)-oxazolone] is shown below.

An azide compound (azide XV) having an azlactone ring was obtained from equimolar amounts of p-azidohippuric acid and cinnamaldehyde in the same manner as in Example 1. This azide XV had a wavelength of maximum photoabsorption at 394 nm in methanol.

Next, preparation of a resist by use of azide XV and confirmation of its photosensitivity are shown below.

A resist solution having the following composition was prepared:

| | |
|---|---|
| Polyvinylphenol (Resin M, Maruzen Oil Co., Ltd.) | 2.5% by weight |
| Azide XV | 0.6% by weight |
| Cyclohexanone | 96.9% by weight. |

This solution was spin-coated on a silicon wafer having a diameter of 3 inches at 100 r.p.m. with infrared radiation, and the cyclohexanone was evaporated to form a resist film of 0.8 μm in thickness. The film was placed at a distance of 50 cm from a 600 W Xe-Hg lamp and exposed to light having a wavelength longer than 430 nm through a UV cut-off filter V-Y43 (Toshiba) to print a pattern. The exposed film was developed with a tetramethylammonium hydroxide (0.95%) aqueous solution at 24° C. for 70 seconds. When the exposure time was 30 seconds, a slight pattern of resist film was observed, while when it was 100 seconds, a clear negative pattern of resist film was obtained at high resolution without swelling.

The wavelength of maximum photo-absorption of a film formed by coating the aforesaid resist solution on a quartz plate was 412 nm.

EXAMPLE 8

First, synthesis of azide XVI [2-(p-azidophenyl)-4-(p-azidocinnamylidene)-5(4)-oxazolone] is shown below.

An azide compound (azide XVI) having an azlactone ring was obtained from equimolar amounts of p-azidohippuric acid and p-azidocinnamaldehyde in the same manner as in Example 1. This azide XVI had a wavelength of maximum photo-abcorption at 412 nm in methanol.

Next, preparation of a resist by use of azide XVI and confirmation of its photosensitivity are shown below.

A resist solution having the following composition was prepared:

| | |
|---|---|
| Cyclized polyisoprene | 9.09% by weight |
| Azide XVI | 0.05% by weight |
| Chlorobenzene | 90.86% by weight. |

This solution was spin-coated on a silicon wafer having a diameter of 3 inches at 3,000 r.p.m., and heated at 80° C. for 20 minutes to evaporate the chlorobenzene, whereby a resist film of 1.2 μm in thickness was formed. The film was placed at a distance of 50 cm from a 600 W Xe-Hg lamp and exposed to print a pattern. The exposed film was developed with xylene for 30 seconds.

When the exposure time was 50 seconds, a slight pattern of resist film was observed, while when it was 200 seconds, a clear negative pattern of resist film was obtained.

The wavelength of maximum photo-absorption of a film formed by coating the aforesaid resist solution on a quartz plate to a thickness of 1.2 μm was 424 nm and the absorbance at this wavelength was 0.11.

EXAMPLE 9

First, synthesis of azide XVII [2-(p-(N-phenylsulfonylamino)phenyl)-4-(p-azidocinnamylidene)-5(4)-oxazolone] is shown below.

An azide compound (azide XVII) having an azlactone ring was obtained from equimolar amounts of p-(N-phenylsulfonylamino)hippuric acid and p-azidocinnamaldehyde in the same manner as in Example 1. This azide XVII had a wavelength of maximum photo-absorption at 415 nm in methanol.

Next preparation of resist by use of azide XVII and confirmation of its photosensitivity are shown below.

A resist solution having the following composition was prepared:

| Polyvinylphenol (Resin M, Maruzen Oil Co., Ltd.) | 3.8% by weight |
|---|---|
| Azide XVII | 1.6% by weight |
| Cyclohexanone | 94.6% by weight. |

This solution was spin-coated on a silicon wafer having a diameter of 3 inches at 100 r.p.m. with infrared radiation, and the cyclohexanone was evaporated to form a resist film of 0.64 μm in thickness. The film was placed at a distance of 50 cm from a Xe-Hg lamp and exposed to light having a wavelength longer than 430 nm through a UV cut-off filter V-Y43 (Toshiba) to print a pattern. The exposed film was developed with a tetramethylammonium hydroxide (0.68%) aqueous solution at 24° C. for 130 seconds. When the exposure time was 10 seconds, a slight pattern of resist film was observed, while when it was 50 seconds, a clear negative pattern of resist film was obtained. Said film was not swollen with the developer either and had high resolution.

The wavelength of maximum photo-absorption of a film formed by coating the aforesaid resist solution on a quartz plate to a thickness of 0.7 μm was 425 nm and the absorbance at this wavelength was 2.4.

EXAMPLE 10

First, synthesis of azide XVIII [2-(styryl)-4-(p-azidobenzylidene)-5(4)-oxazolone] is shown below.

A solution of 25 g of cinnamoyl chloride in 50 g of 1,4-dioxane was mixed with a solution of 15 g of glycine and 8 g of sodium hydroxide in 50 g of water. The temperature of the resulting mixture rose to about 80° C. and then dropped and a white solid precipitated in the mixture. After 20 minutes, the whole mixture became paste. To this mixture was added 200 g of water, and the white solid formed was separated from the mother liquor by filtration and air-dried to obtain 20.8 g of white powder. The powder was crude N-cinnamoylglycine.

With 20.8 g of the aforesaid crude N-cinnamoylglycine were mixed 15.0 g of p-azidobenzaldehyde, 4.0 g of sodium acetate (anhydrous) and 45 ml of acetic anhydride, and the whole of the resulting mixture was heated by using water having a temperature of 90° C. After 3 minutes, a yellowish-brown substance was formed and a yellow solid began to deposit immediately. After 5 minutes, yellow paste was obtained. To the paste was added 250 ml of methanol, after which the yellow solid was separated from the mother liquor by filtration, washed successively with 200 ml of methanol, 200 ml of a sodium hydrogencarbonate (2.5%) aqueous solution and 400 ml of water, and finally air-dried to obtain 15.7 g of yellow powder. The yellow powder was a crude desired compound (azide XVIII). A purified product obtained by purifying this substance by recrystallization from acetone had a wavelength of maximum photo-absorption at 405 nm in a mixture of methanol and benzene (10/1=v/v), and the absorbance at this wavelength was measured to be $5.2 \times 10^4$ cm$^{-1}$.liter.mole$^{-1}$.

Next, preparation of a resist by use of azide XVIII and confirmation of its photosensitivity are shown below.

A resist solution having the following composition was prepared:

| Polyvinylphenol (Resin M, Maruzen Oil Co., Ltd.) | 6.0% by weight |
|---|---|
| Azide XVIII | 0.6% by weight |
| Cyclohexanone | 93.4% by weight. |

This solution was spin-coated on a silicon wafer having a diameter of 3 inches at 200 r.p.m. and the cyclohexanone was evaporated by drying with infrared radiation to form a resist film of 0.83 μm in thickness. In exactly the same manner as in Example 5, the film was exposed to the 436 nm light and developed. In this case, even when the exposure time was 1.5 minutes, a clear negative pattern of resist film was obtained at high resolution.

The absorbance at a wavelength of 436 nm of a film formed by coating the aforesaid resist solution to a quartz plate under the same conditions as described above was 0.90.

EXAMPLE 11

First, synthesis of azide XIX [2-(styryl)-4-(p-azidocinnamylidene)-5-(4)-oxazolone] is shown below.

With 2.0 g of N-cinnamoylglycine synthesized in the same manner as in Example 10 were mixed 1.7 g of p-azidocinnamaldehyde, 0.5 g of sodium acetate (anhydrous) and 7 ml of acetic anhydride, and the whole of the resulting mixture was heated by using water having a temperature of 90° C. After 3 minutes, a dark-orange-colored solution was formed. Then, an orange-colored solid began to precipitate, and after 5 minutes, paste was obtained. The heating was terminated after 5 minutes and the paste was allowed to cool. Then, 10 g of methanol was added to the resultant product to obtain a suspension, which was then filtered, and the precipitate was washed with methanol and air-dried to obtain 3.4 g of an orange-yellow solid. One gram of this solid was recrystallized from methyl ethyl ketone and 2.4 g thereof, i.e., the rest was recrystallized from a mixture of equal volumes of benzene and methanol, whereby 1.4 g of recrystallized and purified azide XIX was obtained. This purified product had a wavelength of maximum photo-absorption of 433 nm in a mixture of equal volumes of benzene and methanol, and the absorbance at this wavelength was measured to be $6.7 \times 10^4$ cm$^{-1}$.mole$^{-1}$.liter.

Next, preparation of a resist by use of azide XIX and confirmation of its photosensitivity are shown below.

A resist solution having the following composition was prepared:

| Polyvinylphenol (Resin M, Maruzen Oil Co., Ltd.) | 6.0% by weight |
|---|---|
| Azide XIX | 0.36% by weight |
| Cyclohexanone | 99.04% by weight. |

This solution was spin-coated on a silicon wafer having a diameter of 3 inches at 200 r.p.m. and the cyclohexanone was evaporated by drying with infrared radiation to form a resist film of 0.59 μm in thickness. In exactly the same manner as in Example 5, the film was exposed to the 436 nm light and developed. In this case, exposure for 6 minutes and development for 20 seconds yielded a clear negative pattern of resist film at high resolution.

In addition to the azide compounds described above, azides V to X, XII, XIII, and XX to XXII were also synthesized in the same manner as in Example 1, and it was confirmed that they also had satisfactory photosensitivity.

Satisfactory results were obtained also when there was used an azide compound of the above general formula other than the aforesaid azides I to XXII.

As is evident from the above explanation, a negative type photoresist having high sensitivity and resolution which is suitable for fabrication of semiconductor devices and the like could be obtained by the combination of the above-mentioned azide compound and a suitable polymer compound. Further, the azlactone ring of the aforesaid azide compound is hydrolyzed by an alkali during development to give a carboxyl group, so that the azide compound became alkali-soluble. Therefore, no scum appears.

What is claimed is:

1. A photosensitive composition for providing a negative-type photoresist which is sensitive to light at 436 nm and which is capable of providing a high resolution image, said composition comprising an admixture of a photosensitive azide compound represented by the formula:

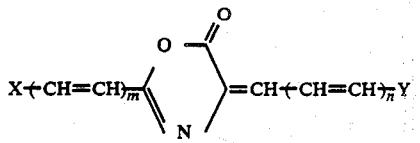

wherein each of X and Y is an aromatic substituent group, at least one of X and Y being a p-azidophenyl group, and n and m are zeros or integers of 1, and a polymeric compound; the amount of azide compound ranging from 0.5 to 100% by weight based on the polymeric compound.

2. A photosensitive composition according to claim 1, wherein both of X and Y in the formula are azidophenyl groups.

3. A photosensitive composition according to claim 1, wherein said polymer compound is at least one polymeric compound selected from the group consisting of products of condensation of phenol derivatives and formaldehyde, and hydroxystyrene polymers.

4. A photosensitive composition according to claim 1, wherein the azide compound has an aromatic substituent group containing no azide group as X and a p-azidaphenyl as Y.

5. A photosensitive composition according to claim 1, wherein the azide compound is at least one member selected from the group consisting of

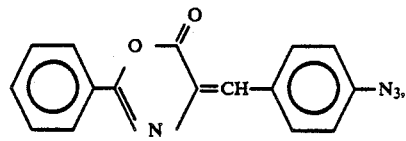
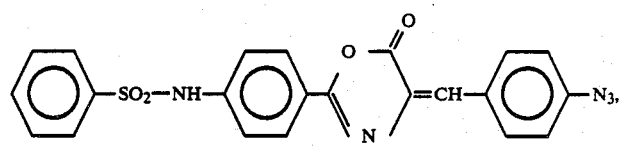

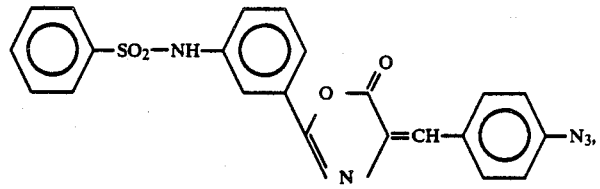

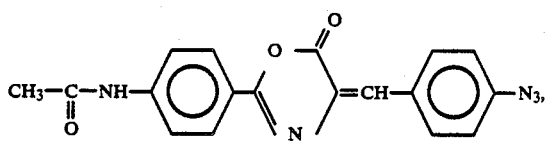
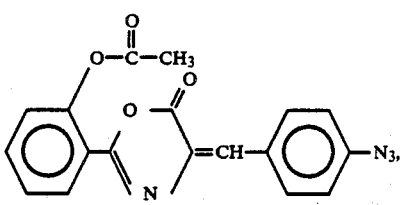

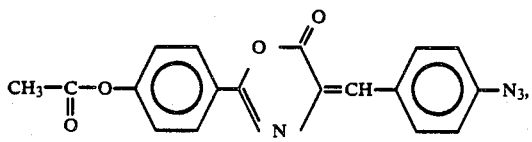
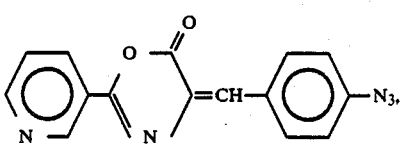

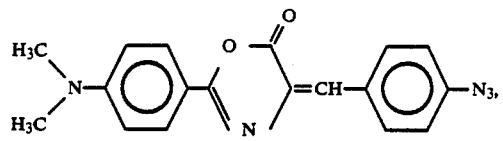
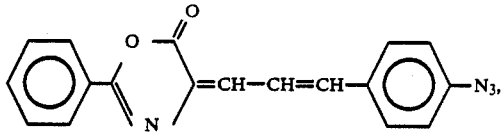
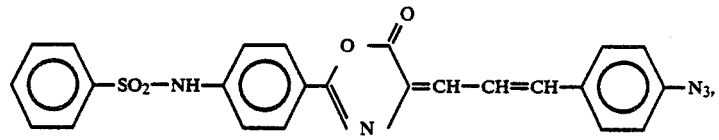
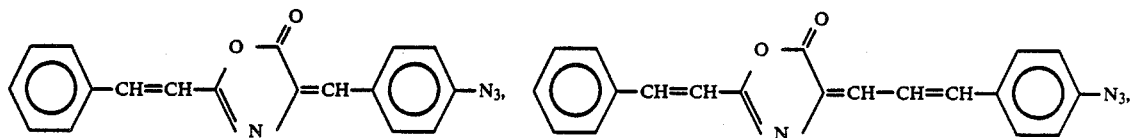
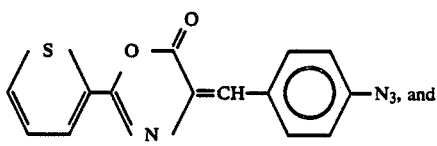, and
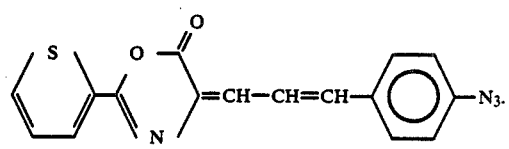.
6. A composition according to claim 1, wherein the one of X and Y which is not a p-azidophenyl group is a group of the formula:
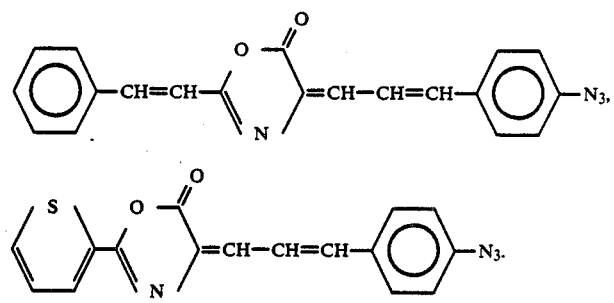
-continued
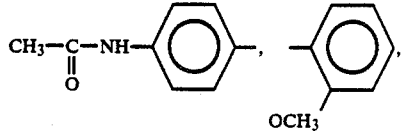
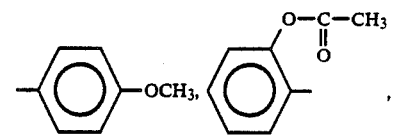
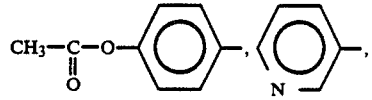
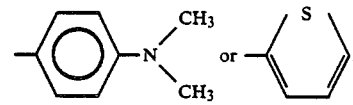
* * * * *